(12) United States Patent
Sharma

(10) Patent No.: US 6,901,295 B2
(45) Date of Patent: May 31, 2005

(54) METHOD AND APPARATUS FOR ELECTRICAL STIMULATION OF THE LOWER ESOPHAGEAL SPHINCTER

(76) Inventor: Virender K. Sharma, 6531 N. 60th St., Paradise Valley, AZ (US) 85253

( * ) Notice: Subject to any disclaimer, the term of this patent is extended or adjusted under 35 U.S.C. 154(b) by 336 days.

(21) Appl. No.: 10/194,371

(22) Filed: Jul. 12, 2002

(65) Prior Publication Data

US 2003/0014086 A1 Jan. 16, 2003

Related U.S. Application Data

(60) Provisional application No. 60/305,516, filed on Jul. 14, 2001.

(51) Int. Cl.[7] .............................................. A61N 1/08
(52) U.S. Cl. ........................................ 607/40; 607/133
(58) Field of Search .................................. 607/40, 133

(56) References Cited

U.S. PATENT DOCUMENTS

| | | | | |
|---|---|---|---|---|
| 4,612,934 A | * | 9/1986 | Borkan | 607/40 |
| 5,117,827 A | * | 6/1992 | Stuebe et al. | 600/350 |
| 5,292,344 A | * | 3/1994 | Douglas | 607/40 |
| 6,097,984 A | * | 8/2000 | Douglas | 607/40 |
| 6,285,897 B1 | * | 9/2001 | Kilcoyne et al. | 600/350 |
| 6,449,511 B1 | * | 9/2002 | Mintchev et al. | 607/40 |

OTHER PUBLICATIONS

Compare Systems: Summary of Neurostimulation Systems Features, Advanced Neuromodulation Systems (ANS) home page, accessed Jul. 24, 2004 from http://www.ans–medical.com/patients/WhichSystemIsBest/SumOfNeurostimulation.html.*

* cited by examiner

Primary Examiner—Jeffrey R. Jastrzab
Assistant Examiner—Alyssa M. Alter
(74) Attorney, Agent, or Firm—Davis Chin

(57) ABSTRACT

A method and apparatus for electrical stimulation of the lower esophageal sphincter (LES) is provided. Electrode sets are placed in the esophagus in an arrangement that induce contractions of the LES by electrical stimulation of the surrounding tissue and nerves. The electrical stimulus is applied by a pulse generator for periods of varying duration and varying frequency so as to produce the desired contractions. The treatment may be short-term or may continue throughout the life of the patient in order to achieve the desired therapeutic effect. The stimulating electrode sets can be used either alone or in conjunction with electrodes that sense esophageal peristalsis. The electrode sets can be placed endoscopically, surgically or radiologically.

15 Claims, 3 Drawing Sheets

METHOD AND APPARATUS FOR ELECTRICAL STIMULATION OF THE LOWER ESOPHAGEAL SPHINCTER

CROSS-REFERENCE TO RELATED APPLICATIONS

This application is a continuation-in-part of provisional application Ser. No. 60/305,516 filed on Jul. 14, 2001.

BACKGROUND OF THE INVENTION

1. Field of the Invention

This invention relates generally to a method and apparatus for electrical stimulation of the esophagus. More particularly, this invention relates to a method and apparatus for electrical stimulation of a portion of the esophagus including the lower esophageal sphincter so as to reduce acid reflux.

2. Description of the Prior Art

As is generally known to those skilled in the art, gastro-esophageal reflux disease (GERD) is a common chronic condition affecting more than 10% of the population in the United States. GERD is associated with significant morbidity and impaired quality of life. This condition results from exposure of esophageal mucosa to gastric acid as the acid refluxes from the stomach into the esophagus. The acid damages the esophageal mucosa resulting in heartburn, ulcers, bleeding, scarring, Barrett's esophagus (pre-cancerous esophageal lining) and adeno-cancer of the esophagus. The incidence of GERD in the United States has risen two to three folds over the last decade.

In the prior art heretofore, acid suppression with medications (H-2 receptor antagonists or proton pump inhibitors) is the mainstay of therapy. Alternatively, open surgical or laparoscopic fundoplication is used in a few patients. However, these procedures all suffer from the disadvantages that they are associated with significant morbidity and small but finite mortality. More recently, there has been an interest which is focused on endoscopic treatments of GERD.

As used herein, the lower esophageal sphincter (LES) is a smooth muscle located between the stomach and the esophagus which acts as a barrier to gastric acid reflux. Transient lower esophageal sphincter relaxation (TLESR) is the major pathogenic mechanism for GERD. Decreased LES tone may also cause or contribute to GERD. Therefore, it would be desirable to prevent relaxation of the LES and/or increase LES tone in order to increase the barrier action of the LES, thereby reducing the exposure of esophageal mucosa to gastric acid reflux. Most of the newer endoscopic techniques of the prior art rely on inducing scarring and/or hypertrophy of LES to reduce or prevent relaxation of the LES by producing injury using radio frequency or thermal ablation. Other prior art procedures have tried to alter the LES by placing mucosal sutures or submucosal injection of silicone in the LES. However, all of these prior art methods suffer from the major disadvantage in that they induce injury. Further, the results are substantially irreversible, and there is limited ability to make adjustments without requiring subsequent endoscopic procedures.

It is also generally known in the art that smooth muscles and associated nerves can be electrically stimulated so as to cause the muscle to contract or relax. For example, it is known in the art to electrically stimulate the heart with an implanted pacemaker for creating contractions at a rate compatible with providing adequate blood supply to the heart. It is further known in the art to artificially propagate contractions of the gastro-intestinal (Gl) tract by implanting electrodes below the LES to facilitate emptying portions of the tract. This latter method uses electrode sets which are placed serially along the Gl tract so as to successively and repetitively stimulate contractions, thereby propagating contents through the tract portion.

SUMMARY OF THE INVENTION

Accordingly, it is a general object of the present invention to provide a method and apparatus of preventing TLESR which overcomes the problems encountered in the prior art methods.

It is an object of the present invention to provide a method and apparatus for increasing lower esophageal sphincter tone.

It is also an object of the present invention to provide a method and apparatus for preventing TLESR and/or increasing lower esophageal sphincter tone without causing permanent injury to the surrounding tissue or organs.

It is another object of the present invention to provide a method and apparatus for preventing TLESR and/or increasing lower esophageal sphincter tone that is controllable by changing the duration, power and frequency of the stimulus without requiring subsequent endoscopic, surgical or radiological procedures.

It is still another object of the present invention is to provide a method and apparatus for treating GERD by providing electrical stimulation to the LES through the use of one or more electrode sets.

In accordance with these aims and objectives, the present invention is concerned with the provision of a method and apparatus for electrical stimulation of the lower esophageal sphincter (LES). Electrode sets are placed in the esophagus in an arrangement that induce contractions of the LES by electrical stimulation of the surrounding tissue, muscles and nerves. The electrical stimulus is applied for periods of varying duration and varying frequency so as to produce the desired contractions. The treatment may be short-term or may continue throughout the life of the patient in order to achieve the desired therapeutic effect. The stimulating electrode sets can be used either alone or in conjunction with other electrodes that sense esophageal peristalsis or esophageal pH. The electrode sets can be placed endoscopically, surgically or radiologically.

BRIEF DESCRIPTION OF THE DRAWINGS

These and other objects and advantages of the present invention will become more fully apparent from the following detailed description when read in conjunction with the accompanying drawings with like reference numerals indicating corresponding parts through-out, wherein.

DESCRIPTION OF THE PREFERRED EMBODIMENTS

Figure 1:
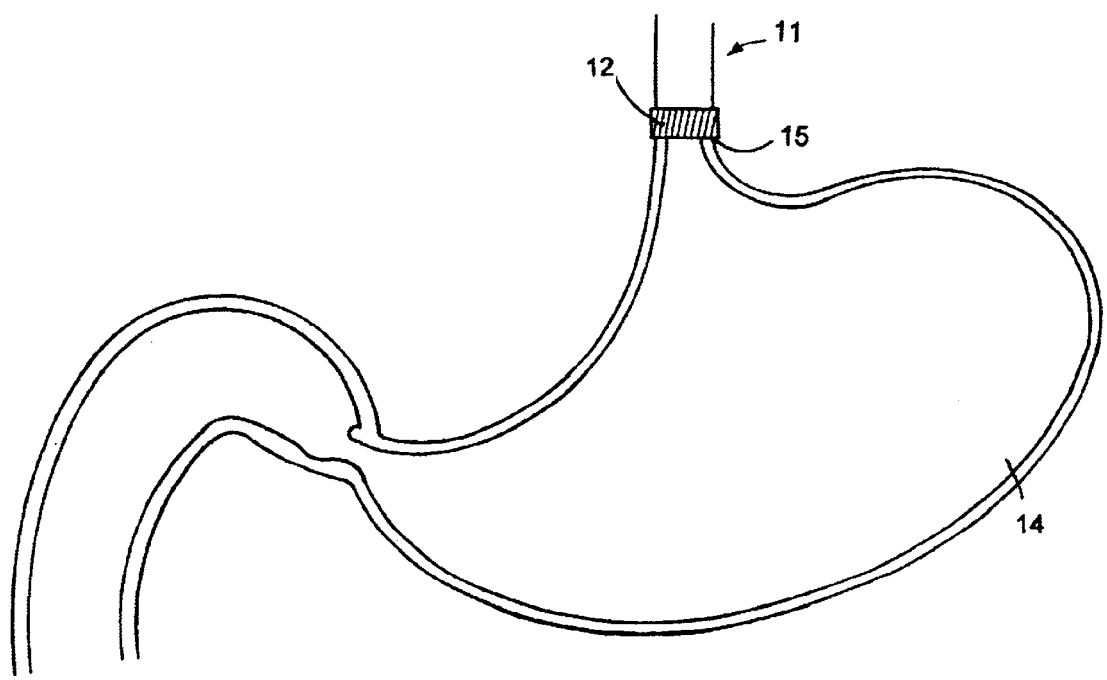
FIG. 1 is a schematic illustration of a portion of the gastro-intestinal tract.

Referring now in detail to the various views of the accompanying drawings, FIG. 1 illustrates a portion of the gastro-intestinal (GI) tract comprised of an esophagus 11, a lower esophageal sphincter (LES) 12, and a stomach 14. The lower esophageal sphincter 12 is interconnected between the esophagus 11 and the stomach 14 and acts as a barrier so as to prevent acid reflux from the stomach to the esophagus. The LES is in tonic contraction but may suffer transient periods of relaxation which allow gastric acids to flow into the esophagus, thereby causing a reflux disorder. In order to reduce acid from reaching the esophageal mucosa, an electrical stimulus is applied to one or more locations in the esophagus preferably within an area approximately 5 cm above the LES to 5 cm below the LES. These stimuli cause contraction of the LES and prevent transient relaxation.

In the preferred embodiments, a plurality of electrode sets are placed in the Gl tract near the LES. Each of the electrode sets is comprised of at least one active electrode and at least one ground electrode. The electrode sets may be arranged in any pattern that produces the desired stimulation to the LES, such as including a circumferential pattern, along a longitudinal axis, irregular or other placement.

Figure 2:
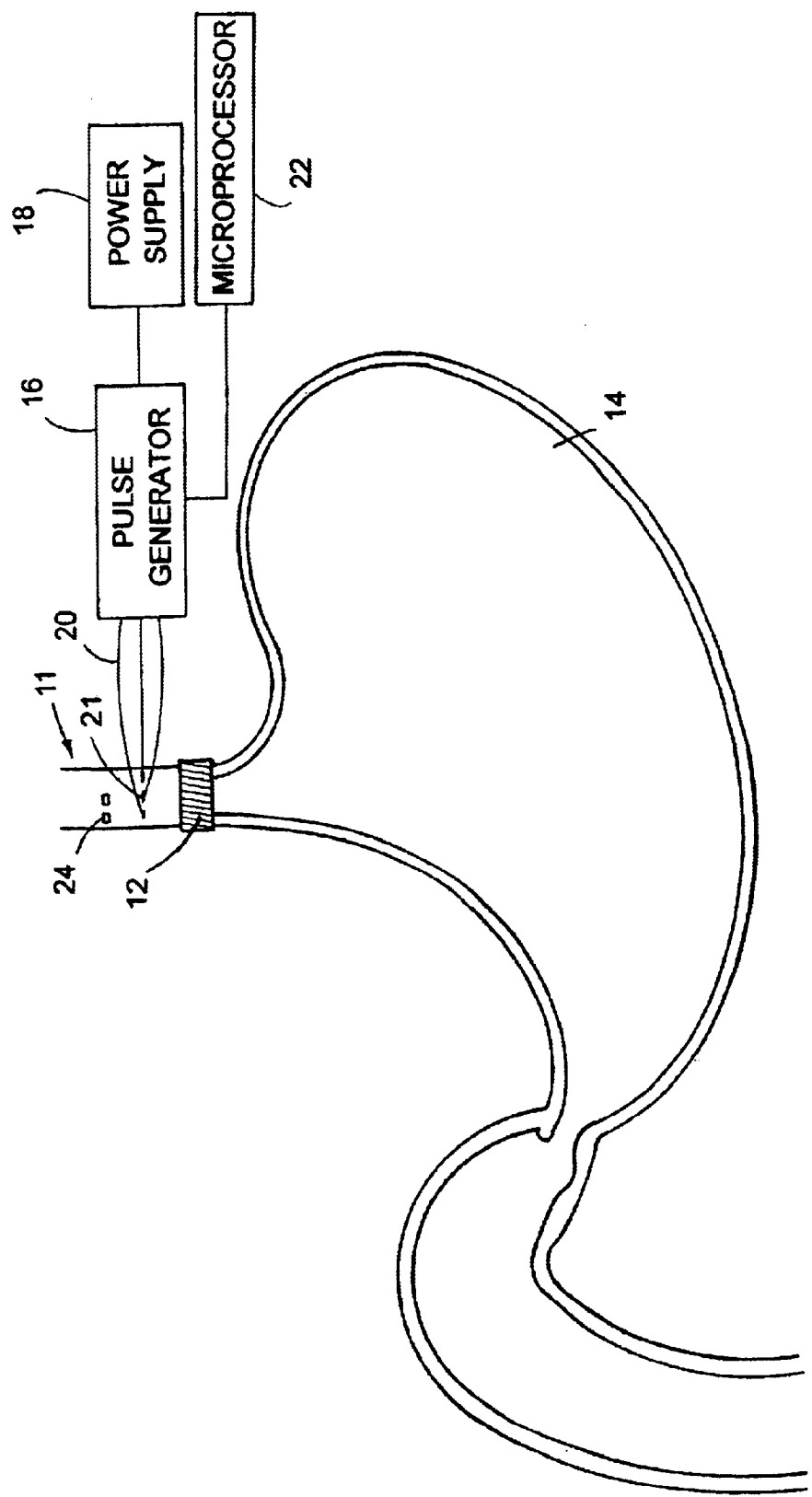
FIG. 2 is a schematic illustration of electrode sets implanted in the esophagus above the lower esophageal sphincter.
Figure 3:
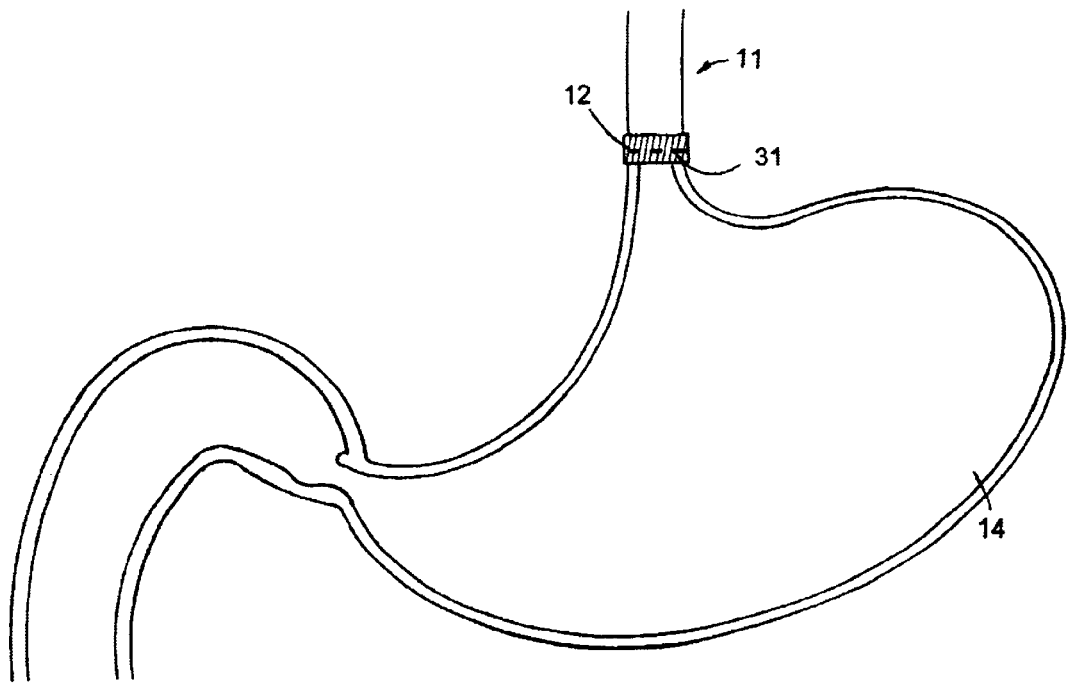
FIG. 3 is a schematic illustration of electrode sets implanted in the esophagus in the lower esophageal sphincter.
Figure 4:
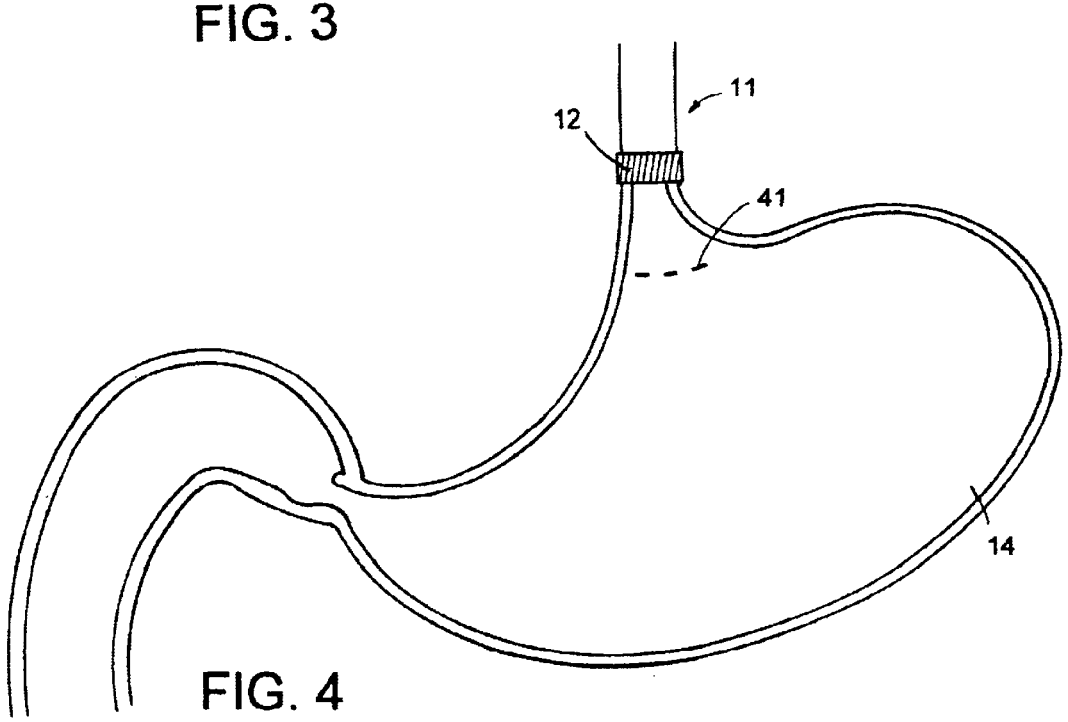
FIG. 4 is a schematic illustration of electrode sets implanted below the esophagus in the lower esophageal sphincter.

In particular, FIG. 2 shows a first preferred embodiment wherein a plurality of electrode sets 21 are placed in a loose linear configuration above the LES 12. FIG. 3 shows a second preferred embodiment in which the plurality of electrode sets 31 are placed in the LES 12. FIG. 4 shows a third preferred embodiment in which the plurality of electrode sets 41 are placed below the LES 12, also in a loose linear configuration. The electrode sets 21, 31, and 41 can be placed in the mucosal, submucosal, muscularis or serosal layer 15 (FIG. 1) of the esophagus 11, LES 12 or stomach 14. The electrode sets can be placed by endoscopic, surgical or radiological procedure.

With reference again to FIG. 2, a device 16 for electrical stimulation of the portion of the GI tract is illustrated which is comprised of a pulse generator. The pulse generator is connected to a power source 18 for supplying a source of power. The pulse generator is further connected to the electrode sets 21 by wires 20 for applying the electrical stimulus to the electrode sets 21.

Alternatively, the electrode sets 21 may be coupled to the pulse generator 16 in a wireless fashion. The power source 18 can be either a direct current source or an alternating current source. The number of electrode sets is determined by a number of factors, including the size of the electrodes, their power, the size of the desired placement area. Preferably, the device 16 is controlled by a microprocessor 22 for applying the electrical stimulus for periods of varying duration and varying power/frequency so as to produce the desired contractions.

Each of the electrode sets provides an electrical stimulus of less than 1 amp. The electrical stimulus can be provided continuously or intermittently, for example one time or more per hour. Over time, stimulation, whether continuous or intermittent, may serve to tone the smooth muscle of the LES. With sufficient tone, further electrical stimulation may be reduced or avoided. GERD may be successfully treated with a single treatment, or life-long stimulation may be required.

The electrical stimulus may have any shape necessary to produce the desired result, including a square, rectangular, sinusoidal, or sawtooth shape. The frequency of the electrical stimulus is in the range of approximately 1–100 Hz. The stimulus may be triggered by a transmitter (not shown) external to the human body, similar to a remote transmitter for a cardiac pacemaker. With appropriate power settings and treatment periods, TLESR is eliminated without causing permanent injury to the surrounding tissue or organs.

Objective measurement of the effects can be made by visual inspection with an endoscope or by insertion of a pH probe to measure the acid reflux or a manometery catheter to measure LES tone and TLESR pH sensors can be included on or in addition to the stimulating electrode sets 21, 31, and 41 to sense changes in esophageal pH due to acid reflux and appropriately modify (increase or decrease) the electrical stimulus.

Additional sensing electrodes 24 (FIG. 2) can be placed in the esophagus to sense esophageal peristalsis. Upon sensing peristalsis, the electrical stimulation of the LES can be inhibited so that the LES can relax and food can pass to the stomach. Control of the LES can also be achieved by turning off the transmitter of the external gastric pacer. The stimulating electrode sets of this invention can be used in combination with additional pacing electrodes, as are known in the art, to treat disorders of gastric emptying.

From the foregoing detailed description, it can be seen that the present invention provides an improved method and apparatus for electrical stimulation of the lower esophageal sphincter. The present invention is achieved by the placement of electrode sets in the esophagus in an arrangement that induce contractions of the lower esophageal sphincter due to electrical stimulation of the surrounding tissue and nerves. The electrical stimulus is applied by a pulse generator for periods of varying duration and varying frequency so as to produce the desired contractions.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

What is claimed is:

1. A method of electrically stimulating the lower esophageal sphincter comprising the steps of:
   a) arranging a plurality of electrode sets within a portion of the gastro-intestinal tract wherein electrical stimuli from the electrode sets causes the lower esophageal sphincter to contract;
   b) applying electrical stimuli the plurality of electrode sets wherein the electrical stimuli prevent transient relaxation of the LES and/or increase the tone of the LES
   c) said plurality of electrode sets for stimulating the lower esophageal sphincter including pH sensors for detecting change in esophageal pH due to acid reflux; and
   d) applying sensing electrodes in the esophagus for detecting esophageal peristalsis so as to inhibit the electrical stimulation of the lower esophageal sphincter in order to pass food to the stomach.

2. A method according to claim 1 wherein the portion of the gastro-intestinal tract is approximately 5 cm above the LES to 5 cm below the LES.

3. A method according to claim 1 wherein the portion of the gastro-intestinal tract is the esophagus.

4. A method according to claim 1 wherein the portion of the gastro-intestinal tract is the lower esophageal sphincter.

5. A method according to claim 1 wherein the electrical stimuli are provided by a pulse generator.

6. A method according to claim 5 wherein the electrical stimuli have shape, which are either square, rectangular, sinusoidal, or sawtooth.

7. A method according to claim 5 wherein the electrical stimuli have a frequency in the range of approximately of 1–100 Hz.

8. A device for electrical stimulation of smooth muscle comprising a portion of the gastrointestinal tract, the device comprising:
 a) a pulse generator for providing electrical stimulation;
 b) a plurality of electrode sets connected to the pulse generator wherein the electrode sets are adapted to be arranged within the portion of the gastrointestinal tract in the area approximately 5 cm above the LES to 5 cm below the LES such that electrical stimulation in the area causes contraction of the lower esophageal sphincter;
 c) said plurality of electrode sets for stimulating the lower esophageal sphincter including pH sensors for detecting change in esophageal pH due to acid reflux; and
 d) sensing electrodes adapted to be disposed in the esophagus for detecting esophageal peristalsis so as to inhibit the electrical stimulation of the lower esophageal sphincter in order to pass food to the stomach.

9. A device according to claim 8 wherein the portion of the gastro-intestinal tract is the esophagus.

10. A device according to claim 9 wherein the electrical stimulation has shapes, which are either square, rectangular, sinusoidal, or sawtooth.

11. A device according to claim 9 wherein the electrical stimulation has a frequency in the range of approximately of 1–100 Hz.

12. A device according to claim 8 wherein the portion of the gastro-intestinal tract is the lower esophageal sphincter.

13. A device according to claim 8 wherein the pulse generator is connected to the electrode sets by wires.

14. A device according to claim 8 wherein the pulse generator is controlled by a microprocessor.

15. A device according to claim 8 wherein the pulse generator is connected to a power source of alternating current.

* * * * *